United States Patent [19]

Dixit et al.

[11] Patent Number: 5,502,076
[45] Date of Patent: Mar. 26, 1996

[54] DISPERSING AGENTS FOR USE WITH HYDROFLUOROALKANE PROPELLANTS

[75] Inventors: Suresh C. Dixit, Neshamic Station; David Goldman, Hillsdale, both of N.J.; John J. Hu, Huntington, Conn.; Krish Sethachutkul, Scarsdale, N.Y.

[73] Assignee: Hoffmann-La Roche Inc., Nutley, N.J.

[21] Appl. No.: 208,164

[22] Filed: Mar. 8, 1994

[51] Int. Cl.⁶ .................................................. A61K 31/21
[52] U.S. Cl. .................. 514/510; 424/43; 424/45; 424/46; 514/458; 514/772; 514/786; 514/975
[58] Field of Search .................. 514/975, 772, 514/786, 458, 510; 424/43, 45, 46

[56] References Cited

U.S. PATENT DOCUMENTS

| | | | |
|---|---|---|---|
| 4,201,778 | 5/1980 | Draper | 424/243 |
| 4,472,393 | 9/1984 | Shapiro | 424/243 |
| 4,525,341 | 6/1985 | Deihl | 514/474 |
| 4,906,453 | 3/1990 | Tsoucalas | 424/47 |
| 4,983,628 | 1/1991 | Frenette et al. | 514/510 |
| 5,124,395 | 6/1992 | Abramowski et al. | 524/462 |
| 5,188,748 | 2/1993 | Arnaud et al. | 252/67 |
| 5,266,308 | 11/1993 | Lee et al. | 424/47 |

FOREIGN PATENT DOCUMENTS

| | | |
|---|---|---|
| 372777 | 11/1989 | European Pat. Off. . |
| 499344 | 11/1989 | European Pat. Off. . |
| 91/04011 | 4/1991 | WIPO . |
| 92/00061 | 1/1992 | WIPO . |

*Primary Examiner*—Ronald W. Griffin
*Attorney, Agent, or Firm*—George M. Gould; George W. Johnston; John P. Parise

[57] ABSTRACT

Vitamin E acetate, $C_3$-linked triesters, glycerin, t-butanol, and transesterified oil/polyethylene glycol are effective dispersing agents for use with hydrofluoroalkanes. Effective amounts of the above are effective in suspending medicaments which are useful in inhalation aerosols, and especially meter-dose inhalers.

14 Claims, 7 Drawing Sheets

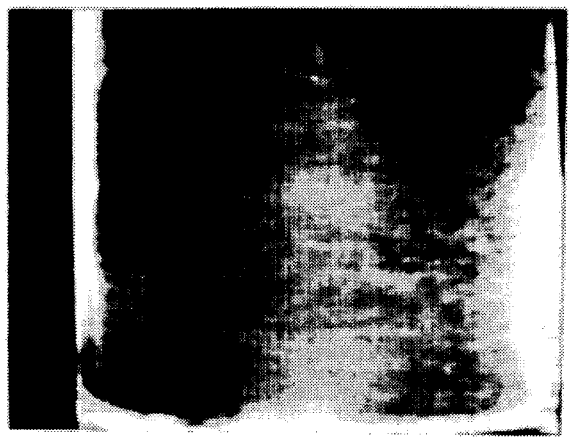
FIG. IA
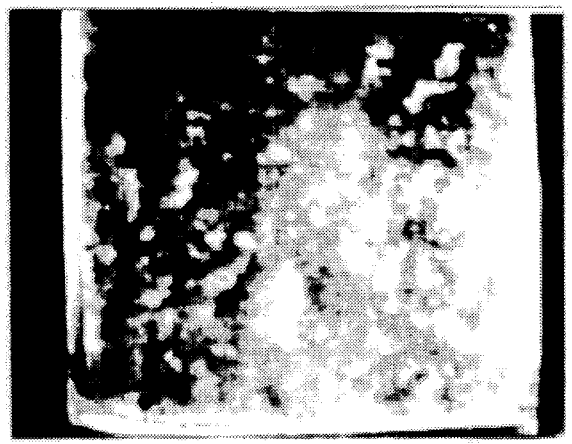
FIG. IB
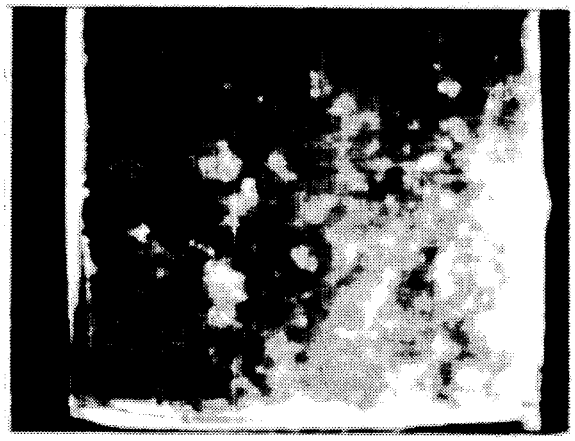
FIG. IC
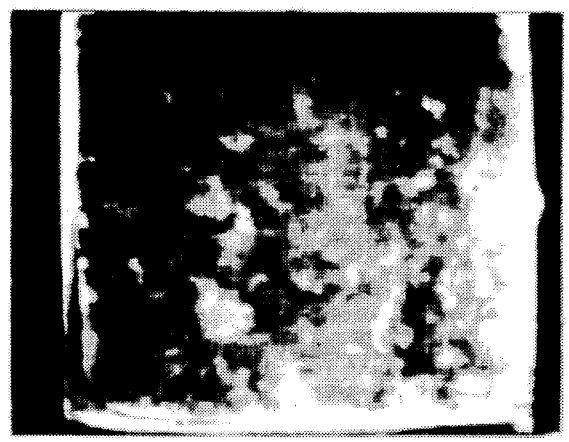
FIG. ID
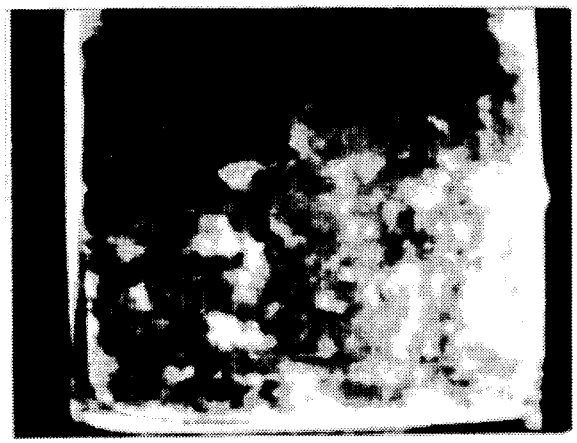
FIG. IE
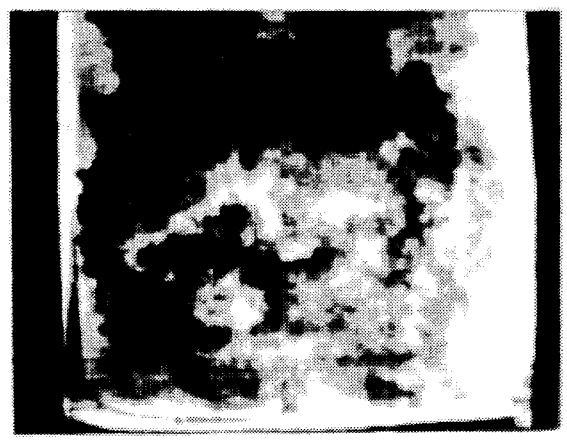
FIG. IF

F I G. 4A
F I G. 4B
F I G. 4C
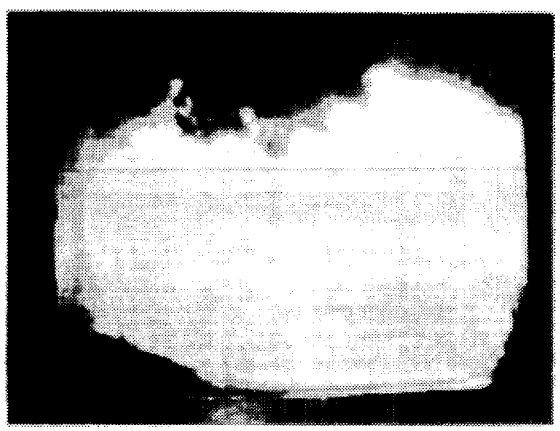
F I G. 4D
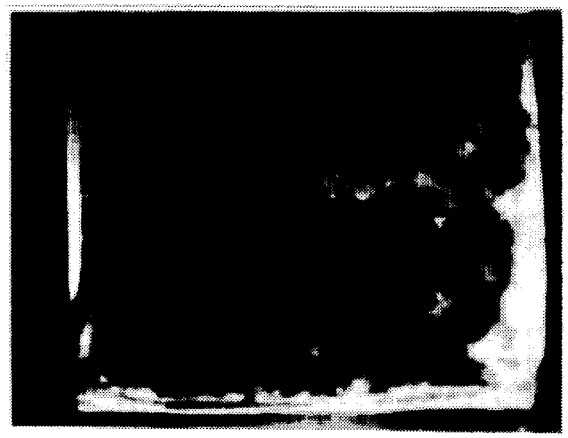
F I G. 4E
F I G. 4F

DISPERSING AGENTS FOR USE WITH HYDROFLUOROALKANE PROPELLANTS

BACKGROUND OF THE INVENTION

1. Field

The invention relates in general to dispersing agents, and more particularly to dispersing agents for suspending medicaments in hydrofluoroalkane (HFA) propellants to be used in inhalation aerosols.

2. Description

There has long been realized a link between chlorofluorocarbons (CFCs) and the depletion of the ozone layer in the earth's atmosphere. Since the Montreal Protocol on Substances That Deplete the Ozone Layer, it has been agreed by most of the world's industrialized nations that the use of chlorofluorocarbons should be eliminated by the year 2000. Recently, parties to the Montreal Protocol voted to advance the deadline for phase out of CFCs to Jan. 1, 1996. Accordingly, there is an ongoing search for non-chlorofluorocarbon propellants.

Hydrofluoroalkanes (HFAs) are one group of aerosol propellants, and ttFA-134a (1,1,1,2-tetrafluoroethane) and HFA-227 (1,1,1,2,3,3,3-heptafluoropropane) have been identified for possible use as replacement propellants in medicament containing aerosols. Unfortunately, neither HFA-134a nor HFA-227 effectively interacts with the dispersing agents currently utilized in pressurized meter dose inhalers (MDIs). Thus, there exists a chasm in adapting these propellants for use in MDIs.

European Patent Publication Numbers 0 499 344 and 0 372 777, the contents of which are herein incorporated by reference, describe aerosol formulations comprising a medicament, HFA-134a, a surfactant, and at least one compound or a co-solvent having a higher polarity than HFA-134a. Surfactants discussed as acceptable in these publications are sorbitan trifoliate, sorbitan monooleate, sorbitan monolaurate, polyoxyethylene (20) sorbitan monolaurate, polyethylene (20) sorbitan monooleate, natural lecithin, oleyl polyoxyethylene (2) ether, stearyl polyoxyethylene (2) ether, lauryl polyoxyethylene (4) ether, block copolymers of oxyethylene and oxypropylene, oleic acid, synthetic lecithin, diethylene glycol dioleate, tetrahydrofurfuryl, oleate, ethyloleate, isopropyl myristate, glyceryl monooleate, glyceryl monostearate, glyceryl monoricinoleate, cetyl alcohol, stearyl alcohol, polyethylene glycol 400, cetyl pyridinium chloride, olive oil, glyceryl monolaurate, corn oil, cotton seed oil, and sunflower seed oil. Such surfactants are also identified in International Publication No. WO 91/04011, the contents of which are herein incorporated by reference.

In another attempt to achieve satisfactory dispersion of a medicament in HFA-134a, the medicament was precoated with a surfactant prior to admixing with the HFA-134a propellant. In particular, micronized beclomethasone dipropionate was coated with Epikuron 200.

In World Patent Publication No. WO 92/00061, the contents of which are herein incorporated by reference, a hydrofluorocarbon propellant was used together with a polyethyloxylated surfactant. Using this surfactant, the formulation was made sufficiently stable without the need for additional solvents.

The present invention provides dispersing agents suitable for suspending medicaments in hydrofluoroalkane compositions. The subject dispersing agents are superior in these properties to those known in the art. Additionally, these dispersing agents provide the advantage of not requiring a co-solvent such as alcohol, thus eliminating the possibility of adverse interaction of alcohol with certain classes of medicaments.

The subject invention fulfills this need through the use of compounds which are generally regarded as safe (GRAS).

SUMMARY OF THE INVENTION

A composition for use in a medicament-containing aerosol comprises a hydrofluoroalkane and a dispersing agent selected from the group consisting of $C_3$-linked triesters, vitamin E acetate, glycerin, t-butanol, and transesterified oil/polyethylene glycol. The dispersing agent is present in an amount effective to suspend the medicament in the hydrofluoroalkane.

BRIEF DESCRIPTION OF THE FIGURES

FIG. 1(A–F) Photographic images of a MDI suspension A at various time points using a $C_8$–$C_{10}$ triglyceride (Neobee M-5 manufactured by Stepan) surfactant. A is at time 0; B is at 15 seconds; C is at 30 seconds; D is at 45 seconds; E is at 1 minute; and F is at 2 minutes.

FIG. 4(A–F) Photographic images of a MDI suspension D at various time points using a sorbitan trioleate surfactant. A is at time 0; B is at 15 seconds; C is at 30 seconds; D is at 45 seconds; E is at 1 minute; and F is at 2 minutes.

DETAILED DESCRIPTION OF THE INVENTION

Figure 2A:
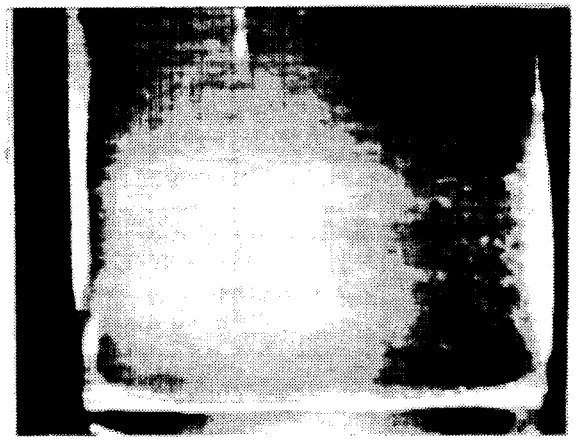
FIG. 2(A–F) Photographic images of a MDI suspension B at various time points using a 1,2,3-propanetriol triacetate (Triacetin) surfactant. A is at time 0; B is at 15 seconds; C is at 30 seconds; D is at 45 seconds; E is at 1 minute; and F is at 2 minutes.
Figure 2B:
Figure 2C:
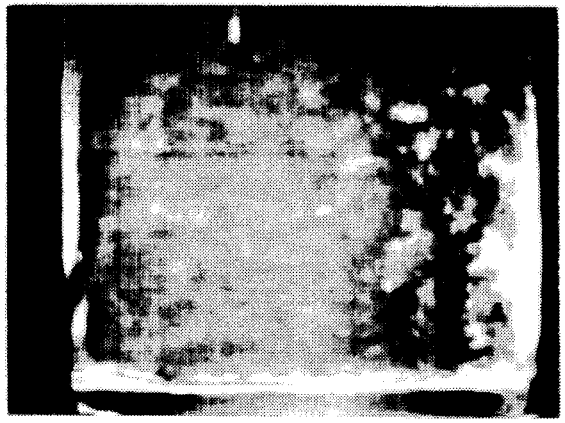
Figure 2D:
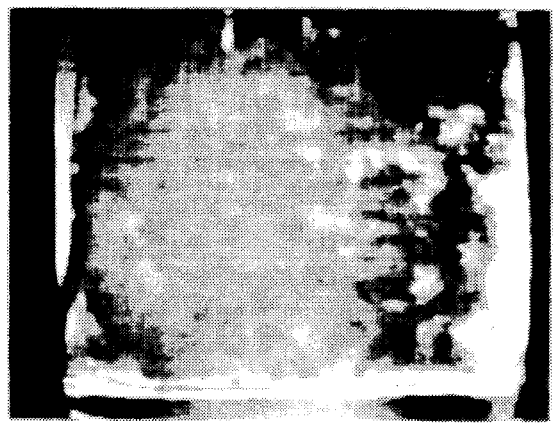
Figure 2E:
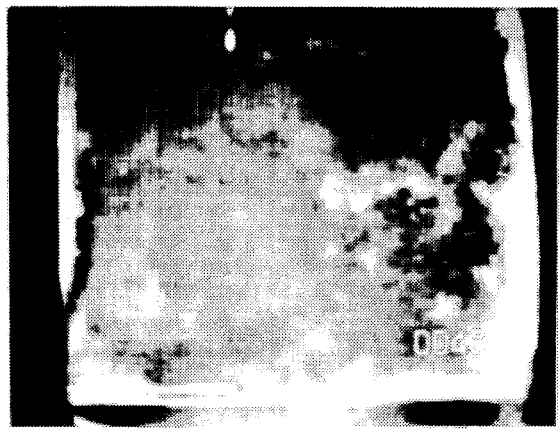
Figure 2F:
Figure 3A:
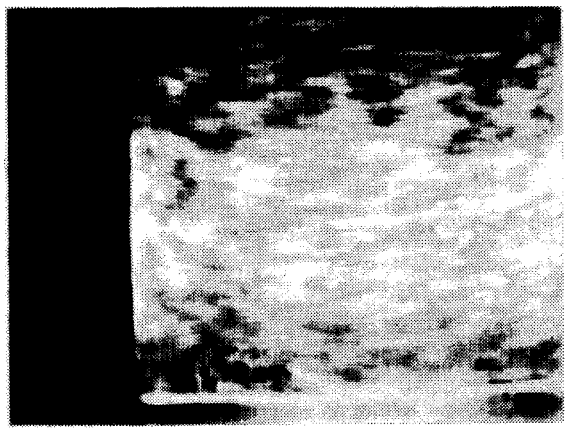
FIG. 3(A–F) Photographic images of a MDI suspension C at various time points using a oleic acid surfactant. A is at time 0; B is at 15 seconds; C is at 30 seconds; D is at 45 seconds; E is at 1 minute; and F is at 2 minutes.
Figure 3B:
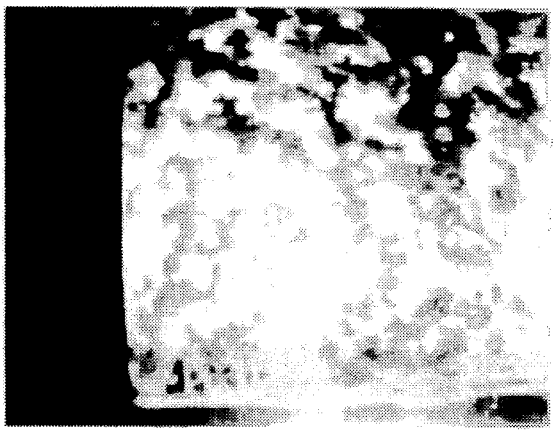
Figure 3C:
Figure 3D:
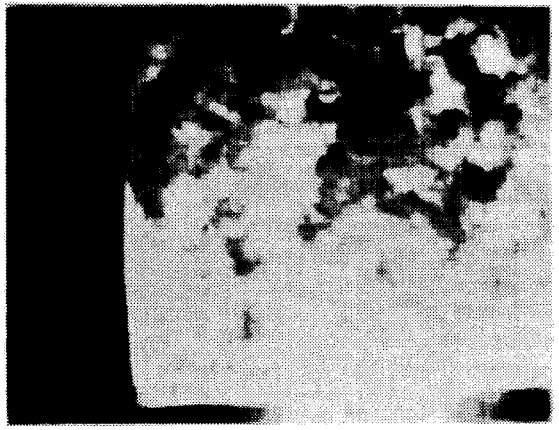
Figure 3E:
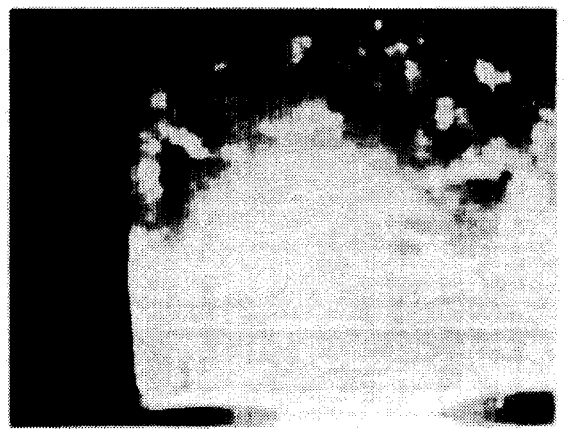
Figure 3F:
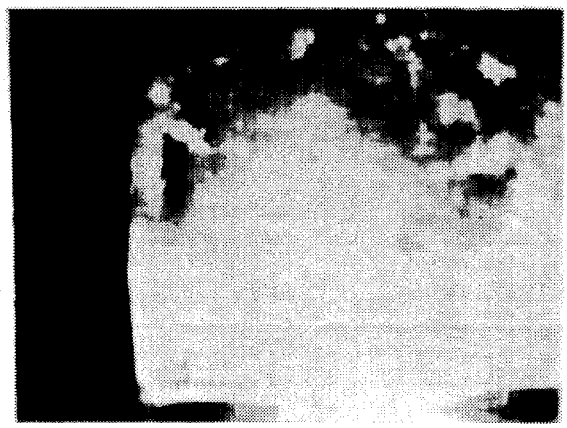

The subject invention will now be described in terms of its preferred embodiments. These embodiments are set forth to aid in the understanding of the invention, but are not to be construed as limiting.

The invention relates to a group of generally regarding as safe (GRAS) materials that are effective as dispersing agents in hydrofluoroalkane (HFA) propellants.

The term "hydrofluoroalkane" includes all $C_1$–$C_5$ polyfluorinated alkane gases which are safe for aerosol administration. Thus far, HFA-134a and HFA-227 appear suitable.

The term "dispersing agents" embraces surfactants and other compositions useful for keeping a medicament suspended in a hydrofluoroalkane. Among the preferred dispersing agents are "$C_3$-linked triesters" having the formula:

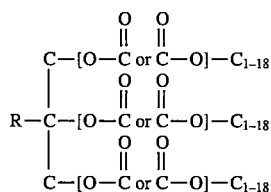

The group R may be hydrogen or hydroxy. In a more preferred embodiment, the $C_{1-18}$ groups are alkyl groups, typically $C_1$ to $C_{10}$ in length. Examples of these $C_3$-linked triesters include $C_8$–$C_{10}$ triglycerides, 1,2,3-propanetriol triacetate and trialkyl citrates. Other suitable dispersing agents include vitamin E acetate, glycerin, t-butanol and transesterified oil/polyethylene glycol (for example, PEG-6).

Preferred $C_8$–$C_{10}$ triglycerides have the formula:

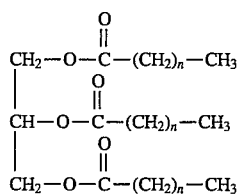

wherein n is 6 or 8. Examples of these triglycerides are Neobee M-5 manufactured by Stepan, Miglyol 810 and 812 manufactured by Huls America, Captex 300 and 355 manufactured by Capital City, Hodag CC-33 manufactured by Hodag, Labrafac Lipophile WL 1349 manufactured by Inolex, Liponate GC manufactured by Lipo, Octanoic/Decanoic Acid Triglyceride O.D.O. manufactured by Nisshin Oil Mill, Protachem CTG manufactured by Protameen, and Unitolate 160-K manufactured by UPI.

Preferred 1,2,3-propanetriol triacetate has the formula:

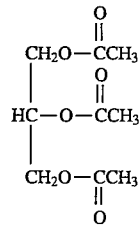

Examples of this compound include ESTOL 1580 manufactured by Unichema and Unitolate GTA manufactured by UPI.

Trialkyl citrates preferrably have the formula:

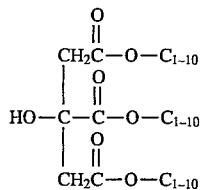

More preferred triaalkyl citrates are triethyl citrate ($C_2$) and tributyl citrate ($C_4$). An example of triethyl citrate is Citroflex 2 manufactured by Morflex.

Transesterified oil/polyethylene glycol is a complex mixture formed from the transesterification of an oil and polyethylene glycol (PEG). These compositions are exemplified by the Labrafil series of compositions manufactured by Gattefosse. For example, Labrafil M 1980 CS (olive oil PEG-6 esters), Labrafil M 1969 CS (peanut oil PEG-6 esters), Labrafil 2125 CS (corn oil PEG-6 esters), Labrafil M 1966 CS (almond oil PEG-6 esters), Labrafil M 1944 CS (apricot kernel oil PEG-6 esters), Labrafil M 2130 CS and BS (Hydrogenated Palm/palm kernel oil PEG-6 esters), Labrafil M 2735 CS (triolein PEG-6 esters), Labrafil Isostearique (tristearin PEG-6 esters) and Labrafil WL 2609 BS (corn oil PEG-8 esters).

The selection of a medicament is within the purview of one skilled in the art. Examples of medicaments include antiallergics, analgesics, antihistamines, antitussives, anginal preparations, antibiotics, anti-inflammatories, bronchodialators, hormones, sulphonamides, therapeutic proteins, peptides, steroids, and mixtures thereof. One particularly suitable group of medicaments are the leukotrine antagonists, which preferably are micronized.

The following examples illustrate the invention. A one-step method for preparing an MDI batch is described in Example 1. The amount of meter-dose drug was quantified with a high pressure liquid chromatograph (HPLC) assay method in Example 2. Particle size and distribution was determined using a laser diffraction method (Malvern particle site analyzer) and a time-of-flight measurement (Aerosizer) in Example 3. Dispersion of the suspension was characterized by image analysis of the particle flocculation in Example 4. Valve performance was measured by shot weight test in Example 5, and valve lubrication was evaluated with an Insiron Materials Tester in Example 6.

EXAMPLE 1

A batch of MDI suspension was prepared and pressure filled as follows: 10.0 g of drug (Ro 24-5913) and 4.0 g of the $C_8$–$C_{10}$ triglyceride dispersing agent (Miglyol 812 Neutral Oil manufactured by Huls America) were placed in a i-liter stainless steel pressure vessel. (Ro 24-5913 is a micronized leukotrine (LTD$_4$) receptor antagonist (E)-4-[3-[2-(4-cyclobutyl-2-thiazolyl)ethenyl]phenylamino] -2,2-diethyl-4-oxobutanoic acid manufactured by Hoffmann La Roche Inc. which has the chemical formula $C_{23}H_{28}N_2O_{3S}$). The vessel was sealed and then charged with 1000 g HFA-134a propellant. The mixture in the vessel was then homogenized at a mixing speed ca. 1,500 rpm for 30 minutes. The resulting suspension contained 1.0% by weight of the drug and 0.4% by weight of the dispersing agent. The mixture was then pressurized to about 230 psi and the vessel connected to a Pamasol aerosol filler. The filler was adjusted so that about 10.0 g of suspension was transferred to a canister crimped with a metering valve at each fill.

EXAMPLE 2

Using the method described in Example 1, a series of suspension formulations containing various amounts of drug and dispersing agent were prepared for aerosol use. Table 1 shows four different formulations (samples A, B, C and D) which were analyzed with a high pressure liquid chromatography HPLC system to determine the uniformity of each dose delivered.

TABLE 1

| Sample | Ro 24-5913 Micronized (mg/Can) | Miglyol 812 (mg/Can) | Vitamin-E Acetate (mg/Can) | HFA-134a (g/Can) |
|---|---|---|---|---|
| A | 100 | 40 | — | q.s. 10.0 g |
| B | 100 | — | 15 | q.s. 10.0 g |
| C | 50 | 40 | — | q.s. 10.0 g |

TABLE 1-continued

| Sample | Ro 24-5913 Micronized (mg/Can) | Miglyol 812 (mg/Can) | Vitamin-E Acetate (mg/Can) | HFA-134a (g/Can) |
|---|---|---|---|---|
| D | 100 | 40 | — | q.s. 10.0 g |

(Throughout the specification similar compositions have been assigned the same sample letter). The aerosol canister was fitted with an actuator to which a collecting device was attached. Total dosage for each can was approximately 150 shots. To obtain a representative dose assay, shot numbers 10, 30, 50, 70, 90, and 110 were collected and analyzed by HPLC assay. Analytical data are shown in Tables 2A, 2B, 2C and 2D. Total dose consists of drug accumulated in the collecting device (Emitted Dose) and drug deposited in the actuator (Actuator). Data demonstrate that a uniform amount of drug was delivered from the beginning through the end stage shots. Total variation as reflected by relative standard deviation (RSD) was less than 4% and 2% for emitted dose and shot weight, respectively. These data indicate the suitability of $C_8$–$C_{10}$ triglycerides for use in aerosol drug delivery.

TABLE 2A

Dose Uniformity Analysis by HPLC
Ro 24-5913 MDI Suspension, Sample A

| Shot Number | Actuator Deposition | Emitted Dose Ro 24-5913 (μg) | Total | Shot Weight (mg) |
|---|---|---|---|---|
| 10 | 70.2 | 672.1 | 742.3 | 61.8 |
| 30 | 120.7 | 662.1 | 782.8 | 62.4 |
| 50 | 122.0 | 667.3 | 789.3 | 61.6 |
| 70 | 150.3 | 671.0 | 821.3 | 62.4 |
| 90 | 136.5 | 665.1 | 801.6 | 62.3 |
| 110 | 111.5 | 690.9 | 802.4 | 61.5 |
| Average | — | 671.4 | 790.0 | 62.0 |
| % RSD | — | 1.5 | 3.4 | 0.7 |

TABLE 2B

Dose Uniformity Analysis by HPLC,
Ro 24-5913 MDI Suspension, Sample B

| Shot Number | Actuator Deposition | Emitted Dose Ro 24-5913 (μg) | Total | Shot Weight (mg) |
|---|---|---|---|---|
| 10 | 121.3 | 562.9 | 684.2 | 61.0 |
| 30 | 116.1 | 578.3 | 694.4 | 62.4 |
| 50 | 142.2 | 571.4 | 713.6 | 63.5 |
| 70 | 134.7 | 605.6 | 740.3 | 63.7 |
| 90 | 158.9 | 572.0 | 730.9 | 63.7 |
| 110 | 172.0 | 569.9 | 741.9 | 64.3 |
| Average | — | 576.7 | 717.6 | 63.1 |
| % RSD | — | 2.6 | 3.4 | 1.9 |

TABLE 2C

Dose Uniformity Analysis by HPLC
Ro 24-5913 MDI Suspension, Sample C

| Shot Number | Actuator Deposition | Emitted Dose Ro 24-5913 (μg) | Total | Shot Weight (mg) |
|---|---|---|---|---|
| 10 | 33.3 | 229.7 | 263.0 | 61.5 |
| 30 | 42.4 | 237.5 | 279.9 | 62.7 |
| 50 | 47.0 | 234.5 | 281.5 | 62.2 |
| 70 | 41.3 | 238.2 | 279.5 | 62.6 |
| 90 | 36.9 | 247.3 | 284.2 | 62.8 |
| 110 | 44.7 | 238.7 | 283.4 | 62.0 |

TABLE 2C-continued

Dose Uniformity Analysis by HPLC
Ro 24-5913 MDI Suspension, Sample C

| Shot Number | Actuator Deposition | Emitted Dose Ro 24-5913 (μg) | Total | Shot Weight (mg) |
|---|---|---|---|---|
| Average | — | 237.7 | 278.6 | 62.3 |
| % RSD | — | 2.4 | 2.8 | 0.8 |

TABLE 2D

Dose Uniformity Analysis by HPLC,
Ro 24-5913 MDI Suspension, Sample D

| Shot Number | Actuator Deposition | Emitted Dose Ro 24-5913 (μg) | Total | Shot Weight (mg) |
|---|---|---|---|---|
| 10 | 69.2 | 659.4 | 728.6 | 61.7 |
| 30 | 107.9 | 677.9 | 785.8 | 60.9 |
| 50 | 123.5 | 717.8 | 841.3 | 62.6 |
| 70 | 138.3 | 701.0 | 839.3 | 62.4 |
| 90 | 100.8 | 718.6 | 819.4 | 60.5 |
| 110 | 115.5 | 683.4 | 798.6 | 62.0 |
| Average | — | 693.0 | 802.2 | 61.7 |
| % RSD | — | 3.4 | 5.3 | 1.3 |

EXAMPLE 3

Using the method of Example 1, a series of suspension formulations containing various amounts of drug and dispersing agent were prepared. Table 3 identifies these aerosol formulations.

TABLE 3

Aerosol Formulation: Samples Prepared for Particle Size Analysis

| Sample | Ro 24-5913, mg/Can (% w/w/) | Vitamin-E Acetate, mg/Can (% w/w) | HFA-134a, g/Can (% w/w) |
|---|---|---|---|
| E | 10.0 (0.1%) | 1.0 (0.01%) | q.s. 10.0 g (99.89%) |
| F | 50 (0.5%) | 50 (0.5%) | q.s. 10.0 g (99%) |
| G | 100 (1.0%) | 50 (0.5%) | q.s. 10.0 g (98.5%) |
| H | 50 (0.5%) | 1.0 (0.01%) | q.s. 10.0 g (99.49%) |

Samples were analyzed for the particle size and distribution using a laser diffraction method (Malvern) and a time-of-flight (Aerosizer) measurement, and the results of these measurements are listed in Tables 4A and 4B. All formulations showed particle sizes within the desirable range of between 0.1 and 10 μm. Particles within this size range are desirable because they can reach the lower respiratory tract and lung alveolar peripherals to maximize the therapeutic effect of the medicine. In Tables 4A and 4B, "D" stands for diameter and "V" stands for volume. The "D(V,n)" numbers relate to particle size diameter in a ranked volume fraction. For example, D(V,0.1) refers to particle diameter at the 10% of the particle size range (smaller than the average particle size), D(V,0.5) is the median particle size; and D(V,0.9) refers to diameter at the 90% particle size range (larger than average particle size). D(4,3) relates to the mean average particle size.

TABLE 4A

Particle Size Analysis Results
Malvern Results (Microns)

| Sample* | D(4,3) | D(V,0.5) | D(V,0.9) | D(V,0.1) |
|---|---|---|---|---|
| E | 6.1 | 1.5 | 8.0 | 0.5 |
| F | 4.8 | 3.0 | 7.1 | 0.8 |
| G | 7.4 | 4.5 | 12.7 | 1.2 |
| H | 6.5 | 3.8 | 12.1 | 1.0 |

*Storage Condition: Initial, Inverted.

TABLE 4B

Aerosizer Diameter (Microns)

| Sample* | D(4,3) | D(V,0.5) | D(V,0.9) | D(V,0.1) |
|---|---|---|---|---|
| E | 1.9 | 1.3 | 3.8 | 0.8 |
| F | 3.4 | 3.1 | 5.2 | 1.8 |
| G | 2.8 | 2.5 | 4.4 | 1.6 |
| H | 1.9 | 1.6 | 3.3 | 1.0 |

*Storage Condition: Initial, Inverted.

These data indicate that vitamin-E acetate is effective in dispersing the drug in suspension for aerosol drug delivery.

EXAMPLE 4

A sample was prepared as follows: 40 mg of micronized drug (Ro 24-5913) and 10 mg of Neobee M-5 were placed in a 15-mL glass vial, which was then crimped with a continuous valve and filled with 10.0 g of HFA-134a propellant under pressure. The vial containing the formulation was then sonicated for 10 minutes. The resulting suspension (designated Sample I) contained 0.4% by weight of the drug, 0.1% by weight of the dispersing agent, and 99.5% of propellant. Similarly, other formulations were prepared:

| Sample | Ro 24-5913 | Surfactant | Propellant |
|---|---|---|---|
| I | 0.4% | Neobee M-5, 0.1% | P134a, q.s. 100% |
| J | 0.4% | Triacetin, 0.1% | P134a, q.s. 100% |
| K | 0.4% | Oleic Acid, 0.1% | P134a, q.s. 100% |
| L | 0.4% | Sorbitan Trioleate, 0.1% | P134a, q.s. 100% |

Each sample was swirled for 5 seconds before being placed in front of a video camera. Image analysis software was used to capture a frame of image at various time points. FIG. 1 shows the images of Sample A at time intervals of 0, 15, 30 and 45 seconds, 1 and 2 minutes. FIGS. 2, 3, and 4 show the images of Samples J, K, and L at the same time points.

These images showed that at a given time interval, formulations containing Neobee M-5 or triacetin were more stable than the formulation containing oleic acid and sorbitan trioleate (STO). Oleic acid and sorbitan trioleate were used extensively as surfactants in CFC suspension formulations. Gross particle agglomeration occurred almost immediately after mixing in the oleic acid and STO formulations. The last two figures graphically illustrate that known surfactants used in CFC propellants can not be effectively used in HFA propellants to sustain a stable suspension.

Using a dispersion index scale from 1 to 4, with 1 being the best dispersed system and 4 being the worst dispersed system, a wide range of formulations containing various agents were screened and ranked. For a formulation to be ranked as having disperion index 1, it must be remained fully dispersed for at least one minute after swirling. Similarly, for a formulation to be ranked as having dispersion index of 2, 3 or 4, it must be remained fully dispersed after swirling for at least 40, 20 and 5 seconds, respectively. Table 5 lists the results and observations.

TABLE 5

Ranking of Dispersion Index for MDI
Formulations Containing Various Surfactants
at the Same Drug Concentration

| Surfactant | Dispersion Index |
|---|---|
| Neobee M5* | 1 |
| Vitamin-E Acetate | 1 |
| Triacetin* | 1 |
| Triethyl Citrate* | 1 |
| Tributyl Citrate* | 1 |
| Glycerin | 1 |
| t-Butanol | 2 |
| Labrafil | 2 |
| Propylene Glycol | 2 |
| Glyceryl Monooleate | 3 |
| Oleyl Alcohol | 3 |
| Oleic Acid | 4 |
| Sorbitan Trioleate | 4 |
| Lecithin | 4 |
| Pluronic 62 | 4 |
| Tween 60 | 4 |
| Span 40 | 4 |

*$C_3$-linked triester

These data indicate that the dispersing agents of the present invention are more effective than known surfactants for keeping a drug suspended in a hydrofluoroalkane propellant.

EXAMPLE 5

Using the method of Example 1, several suspension formulations containing various amounts of drug and dispersing agents were prepared. Table 6 shows the mount (percent by weight based on total weight of the formulation) and type of surface-active dispersing agent used.

TABLE 6

| | Sample | Ro 24-5913 (mg/Can) | Miglyol 812 (mg/Can) | Vitamin-E Acetate, mg/Can | HFA-134a, g/Can |
|---|---|---|---|---|---|
| 1 | A | 100 | 40 | — | q.s. 10.0 g |
| 2 | C | 50 | 40 | — | q.s. 10.0 g |
| 3 | M | 50 | — | 40 | q.s. 10.0 g |
| 4 | N | 50 | 10 | — | q.s. 10.0 g |

Aerosol Formulation (header spanning Ro 24-5913, Miglyol 812, Vitamin-E Acetate, HFA-134a columns)

The above samples were tested for shot weight consistency using a laboratory robotics system. The shot weight testing schedule was as follows in Table 7:

TABLE 7

| Actuation Number | |
|---|---|
| 0–5 | Waste |
| 6–15 | Each Shot was Weighed |
| 16–66 | Waste |
| 68–77 | Each Shot was Weighed |
| 78–127 | Waste |
| 129–138 | Each Shot was Weighed |

Figure 5:
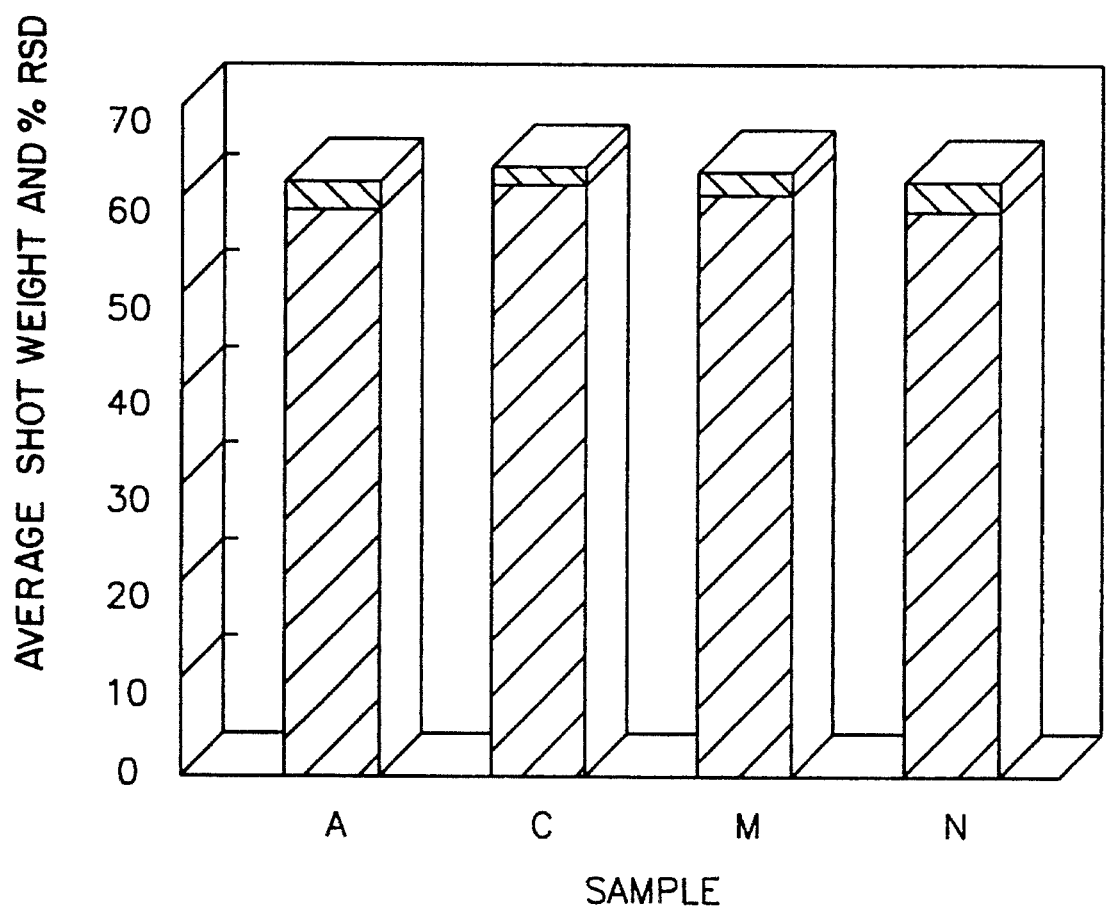
FIG. 5 Bar graph showing average shot weight and relative standard deviation for each sample lot.

A total of 30 shots representing beginning doses (Shot Numbers 6–16), middle doses (Shot Numbers 68–77), and end doses (Shot Numbers 129–138) for each can were weighed and recorded. The average of the 30 shot weights and relative standard deviation (RSD) for each sample were plotted in FIG. 5. The relative standard deviations of all lots were below 5%, showing a satisfactory valve performance and shot weight consistency. These data indicate that vitamin-E acetate and the $C_3$-linked triesters are effective for use in generating uniform shot weights during aerosol drug delivery.

EXAMPLE 6

Using the method of Example 1, several suspension formulations were prepared. Table 8 shows the amount (percent by weight based on total weight of formulation) and type of surface-active dispersing agent used.

TABLE 8

| | Formulation Data Sheet | | |
|---|---|---|---|
| Sample | O | G | Control |
| Ro 24-5913 (% w/w) | 1.0% | 1.0% | — |
| Vitamin-E (% w/w) | — | 0.5% | — |
| HFA-134a | q.s. 100% | q.s. 100% | 100% |
| Energy for Actuation (lb-Inch) (RSD %) | 1.05 (1.9%) | 0.895 (3.4%) | 0.758 (0.7%) |

Figure 6:
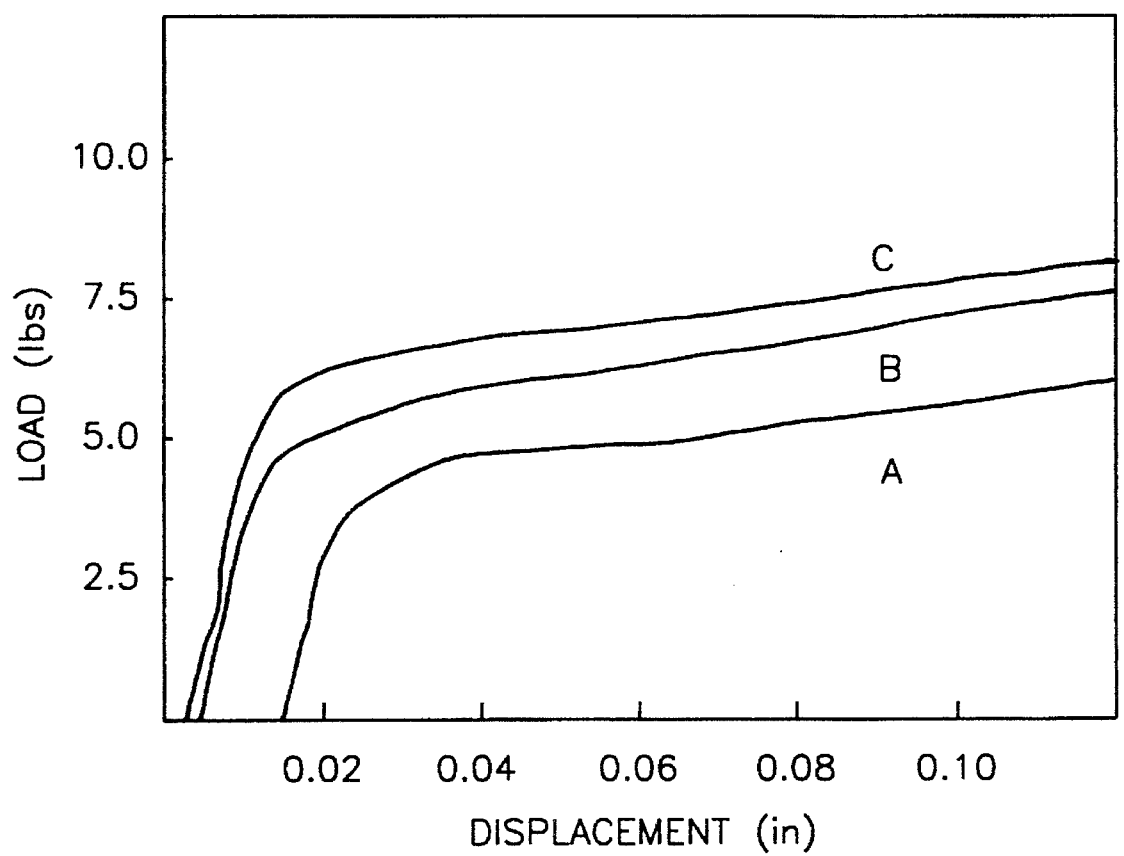
FIG. 6 Graph showing load vs. displacement for three formulations in an inverted metering valve.

The samples prepared above were analyzed by an Inswon Materials Tester to measure the effect of the dispersing agent (here acting more as a metering valve lubricant) on the valve actuation force. FIG. 6 shows the plots of load force versus valve stem displacement. The results indicate that the compressing force increases as the valve is filled with the suspension fluid, largely due to the increase in friction resulting from movement of the stem. By adding the dispersing agent, the compression force is substantially reduced. This advantage is supplemental to increased dispersion of the medicament into the propellant.

Load versus displacement curves of three Bespak BK356 50 mcL inverted metering valves are shown. Curve A represents an empty valve containing no fluid. Curve C represents the same valve containing a suspension HFC-p134a propellant and 1% micronized medicament. Curve B represents the valve containing a suspension identical to that represented in Curve C, except an additional 0.1% Neobee M-5 was added to the suspension.

Figure 7:
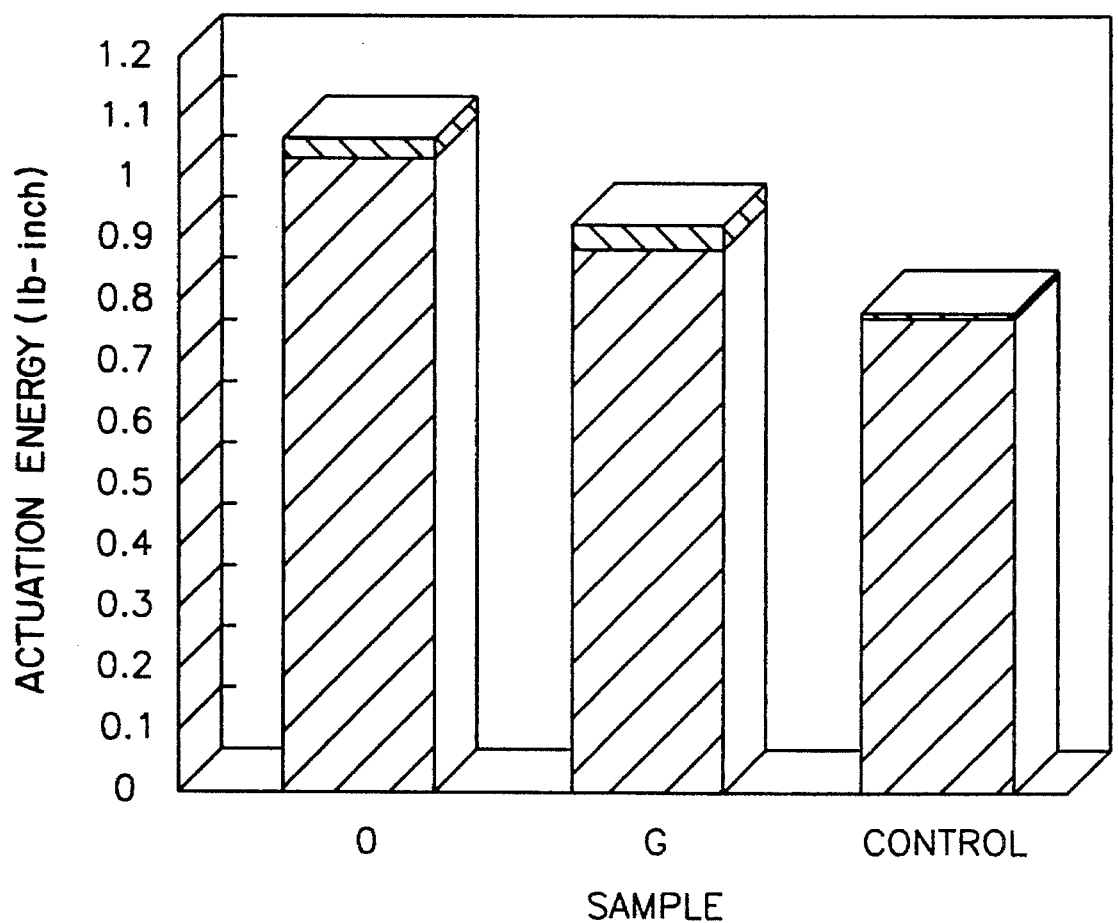
FIG. 7 Bar graph showing total energy for actuating values using different formulations.

FIG. 7 compares total energy required to actuate the valves in different formulations. As is shown by these data, the dispersing agents of the present invention are effective in reducing friction and facilitating aerosol drug delivery.

As shown and exemplified, the dispersing agents of the present invention are useful for dispersing medicaments in hydrofluoroalkanes, and are effective in lubricating the stem to facilitate actuation of the valve.

The invention has been described in terms of its preferred embodiment. However, upon reading the above description, various alternative embodiments will become obvious to those skilled in the art. These variations are to be considered within the scope and spirit of the subject invention, which is only to be limited by the claims which follow and their equivalents.

What is claimed:

1. A composition which comprises a hydrofluoroalkane, a leukotrine antagonist present at about 0.01% by weight to about 2.0% by weight of the composition, and a dispersing agent present at from about 0.01% by weight to about 1.0% by weight of the composition, the dispersing agent being selected from the group consisting of $C_3$-linked triesters, vitamin E acetate, glycerin, t-butanol, and transesterified oil/polyethylene glycol.

2. The composition of claim 1, wherein the $C_3$-linked triester is selected from the group consisting of $C_8$–$C_{10}$ triglycerides, 1,2,3-propanetriol triacetate, and trialkyl citrates.

3. The composition of claim 2, wherein the dispersing agent is a $C_8$–$C_{10}$ triglyceride.

4. The composition of claim 2, wherein the dispersing agent is 1,2,3-propanetriol triacetate.

5. The composition of claim 2, wherein the dispersing agent is a trialkyl citrate.

6. The composition of claim 5, wherein the trialkyl citrate is selected from the group consisting of triethyl citrate and tributyl citrate.

7. The composition of claim 1, wherein the dispersing agent is selected from the group consisting of $C_3$-linked triesters, vitamin E acetate, and glycerin.

8. The composition of claim 7, wherein the dispersing agent is vitamin E acetate.

9. The composition of claim 7, wherein the dispersing agent is glycerin.

10. The composition for claim 1, wherein the dispersing agent is t-butanol.

11. The composition of claim 1, wherein the dispersing agent is transesterified oil/polyethylene glycol-6.

12. The composition of claim 1, wherein the hydrofluoroalkane is selected from the group consisting of 1,1,1,2,3,3,3-heptafluoropropane and 1,1,1,2-tetrafluoroethane.

13. The composition of claim 1, wherein the leukotrine antagonist is a micronized leukotrine antagonist.

14. A method for suspending leukotrine antagonist within a hydrofluoroalkane propellant to form a composition, which comprises:
  (a) selecting a dispersing agent from the group consisting of $C_3$-linked triesters, vitamin E acetate, glycerin, t-butanol, and transesterified oil/polyethylene glycol; and
  (b) mixing the leukotrine antagonist and the selected dispersing agent with the hydrofluoroalkane propellant to form a suspension, the leukotrine antagonist representing from about 0.01% to about 2.0% by weight of the composition and the dispersing agent representing from about 0.01% to about 1.0% by weight of the composition.

* * * * *